(12) United States Patent
Mansfield et al.

(10) Patent No.: US 7,657,304 B2
(45) Date of Patent: Feb. 2, 2010

(54) IMAGING DEVICE FOR RADIATION TREATMENT APPLICATIONS

(75) Inventors: Stan Mansfield, Sunnyvale, CA (US); Robert Kopels, Cupertino, CA (US); Ulrich Martin Graf, Mettmenstetten (CH)

(73) Assignee: Varian Medical Systems, Inc., Palo Alto, CA (US)

( * ) Notice: Subject to any disclaimer, the term of this patent is extended or adjusted under 35 U.S.C. 154(b) by 1068 days.

(21) Appl. No.: 10/264,630

(22) Filed: Oct. 5, 2002

(65) Prior Publication Data

US 2004/0068169 A1 Apr. 8, 2004

(51) Int. Cl.
*A61B 5/05* (2006.01)
*A61B 6/00* (2006.01)
*A61N 5/10* (2006.01)
*H05G 1/02* (2006.01)

(52) U.S. Cl. .............................. 600/427; 378/9; 378/65; 378/197

(58) Field of Classification Search ................. 600/411, 600/425, 427; 378/9, 65, 197
See application file for complete search history.

(56) References Cited

U.S. PATENT DOCUMENTS

| | | | |
|---|---|---|---|
| 3,133,227 A | 5/1964 | Brown et al. |
| 3,144,552 A | 8/1964 | Schonberg |
| 3,193,717 A | 7/1965 | Nunan |
| 4,149,247 A | 4/1979 | Pavkovich et al. |
| 4,149,248 A | 4/1979 | Pavkovich et al. |
| 4,208,675 A | 6/1980 | Bajon et al. |
| 4,209,706 A | 6/1980 | Nunan |
| 4,349,917 A | 9/1982 | Moore |
| 4,521,808 A | 6/1985 | Ong et al. |
| 4,593,967 A | 6/1986 | Haugen |
| 4,675,731 A | 6/1987 | Takasu et al. |
| 4,679,076 A | 7/1987 | Vikterlof et al. |
| 4,726,046 A | 2/1988 | Nunan |
| 4,741,621 A | 5/1988 | Taft et al. |
| 4,825,393 A | 4/1989 | Nishiya |
| 4,853,777 A | 8/1989 | Hupp |
| 4,868,844 A | 9/1989 | Nunan |
| 5,027,818 A | 7/1991 | Bova et al. |

(Continued)

FOREIGN PATENT DOCUMENTS

DE 42 23 488 A1 1/1994

(Continued)

OTHER PUBLICATIONS

Balter, James M. et al., "Daily Targeting of Intrahepatic Tumors for Radiotherapy," Int. J. Radiation Oncology Biol. Phys., vol. 52, No. 1 (2002), pp. 266-271.

(Continued)

*Primary Examiner*—Eric F Winakur
*Assistant Examiner*—Michael T Rozanski
(74) *Attorney, Agent, or Firm*—Blakely, Sokoloff, Taylor & Zafman LLP (57) ABSTRACT

A radiotherapy clinical treatment machine is described having a rotatable gantry and an imaging device with articulating robotic arms to provide variable positioning and clearance for radiation treatment applications. According to one aspect of the invention, a first and a second robotic arms are pivotally coupled to the rotatable gantry, allowing the robotic arms to maneuver independently from the rotatable gantry.

47 Claims, 5 Drawing Sheets

U.S. PATENT DOCUMENTS

| | | | |
|---|---|---|---|
| 5,080,100 | A | 1/1992 | Trotel |
| 5,099,505 | A | 3/1992 | Seppi et al. |
| 5,117,445 | A | 5/1992 | Seppi et al. |
| 5,168,532 | A | 12/1992 | Seppi et al. |
| 5,233,990 | A * | 8/1993 | Barnea ........................ 600/427 |
| 5,335,255 | A | 8/1994 | Seppi et al. |
| 5,394,452 | A | 2/1995 | Swerdloff et al. |
| 5,438,991 | A | 8/1995 | Yu et al. |
| 5,471,516 | A | 11/1995 | Nunan |
| 5,537,452 | A | 7/1996 | Shepherd et al. |
| 5,692,507 | A | 12/1997 | Seppi et al. |
| 5,751,781 | A | 5/1998 | Brown et al. |
| 5,956,382 | A | 9/1999 | Wiener-Avnear et al. |
| 6,031,888 | A * | 2/2000 | Ivan et al. ...................... 378/20 |
| 6,041,097 | A | 3/2000 | Roos et al. |
| 6,104,778 | A | 8/2000 | Murad |
| 6,104,780 | A | 8/2000 | Hanover et al. |
| 6,144,875 | A | 11/2000 | Schweikard et al. |
| 6,222,901 | B1 | 4/2001 | Meulenbrugge et al. |
| 6,275,564 | B1 * | 8/2001 | Ein-Gal ........................ 378/68 |
| 6,307,914 | B1 | 10/2001 | Kunieda et al. |
| 6,318,892 | B1 | 11/2001 | Suzuki et al. |
| 6,325,537 | B1 * | 12/2001 | Watanabe ................... 378/197 |
| 6,325,758 | B1 | 12/2001 | Carol et al. |
| 6,345,114 | B1 | 2/2002 | Mackie et al. |
| 6,370,421 | B1 | 4/2002 | Williams et al. |
| 6,381,302 | B1 | 4/2002 | Berestov |
| 6,385,286 | B1 | 5/2002 | Fitchard |
| 6,429,578 | B1 | 8/2002 | Danielson et al. |
| 6,508,586 | B2 | 1/2003 | Oota |
| 6,842,502 | B2 | 1/2005 | Jaffray et al. |
| 6,888,919 | B2 * | 5/2005 | Graf ............................ 378/65 |
| 6,914,959 | B2 | 7/2005 | Bailey et al. |
| 2001/0001807 | A1 | 5/2001 | Green |
| 2001/0008271 | A1 | 7/2001 | Ikeda et al. |
| 2003/0007601 | A1 | 1/2003 | Jaffray et al. |

FOREIGN PATENT DOCUMENTS

| | | |
|---|---|---|
| DE | 196 14 643 A1 | 10/1997 |
| EP | 0062941 B1 | 9/1984 |
| EP | 0205720 A1 | 12/1986 |
| EP | 0220501 | 5/1987 |
| EP | 0480035 B1 | 11/1994 |
| FR | 2 269 745 | 11/1975 |
| FR | 2 551 664 | 3/1985 |
| GB | 1328033 | 8/1973 |
| JP | 01288241 | 11/1980 |
| JP | HEI 5-57028 | 3/1993 |
| JP | 11155851 | 6/1999 |
| JP | 2000176029 | 6/2000 |
| WO | WO 85/03212 A1 | 8/1985 |
| WO | WO-0057785 | 10/2000 |
| WO | WO-0112066 | 2/2001 |
| WO | WO-0160236 | 8/2001 |

OTHER PUBLICATIONS

Swindell, William et al., "Computed Tomography With a Linear Accelerator With Radiotherapy Applications," Med. Phys., vol. 10, No. 4, Jul./Aug. 1983; pp. 416-420.

Mosleh-Shirazi, Mohammad Amin et al., "A Cone-Beam Megavoltage CT Scanner for Treatment Verification in Conformal Radiotherapy," Radiotherapy and Oncology, vol. 48 (1998), pp. 319-328.

Midgley, S. et al., "A Feasibility Study for Megavoltage Cone Beam CT Using A Commercial EPID," Phys. Med. Biol., vol. 43 (1998), pp. 155-169.

Ruchala, K.J. et al., "Megavoltage CT on a Tomotherapy System," Phys. Med. Biol., vol. 44 (1999), pp. 2597-2621.

Nakagawa, Keiichi, M.D. et al., "Megavoltage CT-Assisted Stereotactic Radiosurgery for Thoracic Tumors: Original Research in the Treatment of Thoracic Neoplasms," Int. J. Radiation Oncology Biol. Phys., vol. 48, No. 2, (2000), pp. 449-457.

Groh, B.A. et al., "A Performance Comparison of Flat-Panel Imager-Based MV and kV Conebeam CT," Med. Phys., vol. 29, No. 6, Jun. 2002, pp. 967-975.

Uematsu, Minoru et al., "Daily Positioning Accuracy of Frameless Stereotactic Radiation Therapy With a Fusion of Computed Tomography and Linear Accelerator (FOCAL) Unit: Evaluation of Z-Axis With a Z-Marker," Radiotherapy and Oncology, vol. 50, No. 3, Mar. 1999, pp. 337-339.

Uematsu, Minoru, M.D. et al., "A Dual Computed Tomography Linear Accelerator Unit for Stereotactic Radiation Therapy: A New Approach Without Cranially Fixated Stereotactic Frames," Int. J. Radiation Oncology Biol. Phys., vol. 35, No. 3 (1996), pp. 587-592.

Uematsu, Minoru, M.D. et al, "Intrafractional Tumor Position Stability During Computed Tomography (CT)-Guided Frameless Stereotactic Radiation Therapy for Lung or Liver Cancers With a Fusion of CT and Linear Accelerator (FOCAL) Unit," Int. J. Radiation Oncology Biol. Phys., vol. 48, No. 2 (2000), pp. 443-448.

Jaffray, David A., Ph.D. et al., "A Radiographic and Tomographic Imaging System Integrated Into a Medical Linear Accelerator for Localization of Bone and Soft-Tissue Targets," Int. J. Radiation Oncology Biol. Phys., vol. 45, No. 3 (1999), pp. 773-789.

Pisani, Laura, M.S. et al., "Setup Error in Radiotherapy: On-line Correction Using Electronic Kilovoltage and Megavoltage Radiographs," Int. J. Radiation Oncology Biol. Phys., vol. 47, No. 3 (2000), pp. 825-839.

Drake, D.G. et al, "Characterization of a Fluoroscopic Imaging System for kV and MV Radiography," Med. Phys., vol. 27, No. 5, May 2000, pp. 898-905.

Jaffray, D.A. and Siewerdsen, J.H., "Cone-Beam Computed Tomography with a Flat-Panel Imager: Initial Performance Characterization," Med. Phys., vol. 27, No. 6, Jun. 2000, 1311-1323.

Fahrig, R. and Holdsworth, D. W., "Three-Dimensional Computed Tomographic Reconstruction Using a C-Arm Mounted XRII: Image Based Correction of Gantry Motion Nonidealities," Med. Phys., vol. 27, No. 1, Jan. 2000, pp. 30-38.

Feldkamp, L.A. et al. "Practical Cone-Beam Algorithm," J. Opt. Soc. Am. A., vol. 1, No. 6, Jun. 1984; pp. 612-619.

Siewerdsen, Jeffery H. and Jaffray, David A., "Optimization of X-Ray Imaging Geometry (With Specific Application to Flat-Panel Cone-Beam Computed Tomography)," Med. Phys., vol. 27, No. 8, Aug. 2000, pp. 1903-1914.

Siewerdsen, Jeffery H. and Jaffray, David A., "Cone-Beam Computed Tomography With a Flat-Panel Imager: Magnitude and Effects of X-Ray Scatter," Med. Phys., vol. 28, No. 2, Feb. 2001, pp. 220-231.

Cho, Paul S. et al., "Cone-Beam CT for Radiotherapy Applications," Phys. Med. Biol., vol. 40 (1995), pp. 1863-1883.

Ragan, "Correction for Distrotion in a Beam Outline Transfer Device in Radiotherapy CT-Based Simulation", Med. Phys. 20 (1), Jan./Feb. 1993, pp. 179-185.

Kuhn, "AIM Project A2003: COmputer VIsion in RAdiology (COVIRA)", Computer Methods and Programs in Biomedicine, 1994, Citation from Dissertation Abstracts, 1 page.

Keys, A CCTV-Microcomputer Biostereometric System for Use in Radiation Therapy (Topography, Medical Physics, Tissue Compensators), 1984, Citation from Energy Science and Technology, 1 page.

Kutcher et al., "Three dimensional radiation treatment planning", Citation from Engineering Index, 1988, 2 pages.

Redpath, et al., "Use of a Simulator and Treatment Planning Computer as a CT Scanner for Radiotherapy Planning", 1984, Citation from Inspec., 1 page.

Elliott, "Interactive Image Segmentation for Radiation Treatment Planning", IBM Systems Journal, 1992, Citation from Medline (R) Database, 1 page.

Kushima et al., "New Development of Integrated CT Simulation System for Radiation Therapy Planning", Kobs J Med Sci., 1993, Citation from Medline (R) Database, 1 page.

Gademann et al., "Three-Dimensional Radiation Planning. Studies on Clinical Integration", Strahlenther Onkol, 1993, 1 page.

Ragan, "Correction for Distortion in a Beam Outline Transfer Device in Radkotherapy CT-based Simulation", Med Phys., 1993, 1 page.

Andrew et al., "A Video-Based Patient Contour Acquisition System for the Design of Radiotherapy Compensators", Med Phys., 1989, 1 page.

Reynolds, "An Algorithm for Three-Dimensional Visualization of Radiation Therapy Beams", Med Phys., 1988, 1 page.

Mohan, "Intersection of Shaped Radiation Beams with Arbitrary Image Sections", Comput Methods Programs Biomed, 1987, 1 page.

Brewsterfuauf, "Automatic Generation of Beam Apertures", Medical Physics, 1993, 1 page.

Hara et al., "Radiotherapeutic System", 00480035/EP-B1, Citation from World Patent, 1994, 1 page.

Moore, "Radiation Image Generating System and Method", 1992020202/WO-A1, 1992, 1 page.

Seppi, "Computed Tomography Apparatus Using Image Intensifier Detector", 1992000567/WO-A1, 1 page.

Bova, "Dosimetric Technique for Stereotactic Radiosurgery", 1990014129/WO-A1, 1990, 1 page.

Kazufumi, "Radiation Treatment Device", 05057028 JP, 1993, 1 page.

Inamura, "CT Simulator For Radiotherapy", 63294839 JP, 1988, 1 page.

Moore, "Radiation Image Generating System and Method", Citation from US Patent, Issued 1993, 2 pages.

Nishihara, "Therapeutic Apparatus", Issued 1991, 2 pages.

Jaffray, "Cone-Beam CT: Application in Image Guided External Beam Radiotherapy and Brachytherapy", IEEE, 2000, 2 pages.

Ning et al., "An Image Intensifier-Based Volume Tomographic Angiography Imaging System: System Evaluation," SPIE, vol. 2432, pp. 280-290.

"Advanced Workstation for Irregular Field Simulation and Image Matching", Copyright 1999, MDS Nordion, 7 pages.

Masahiro et al., "Patient Beam Positioning System Using CT Images", Phys. Med. Biol., 1982, vol. 27, No. 2, pp. 301-305, printed in Great Britain.

Jaffray, David A. et al., "Flat-Panel Cone-Beam Computed Tomography for Image-Guided Radiation Therapy", Int. J. Radation Oncology Biol. Phys., vol. 53, No. 5 (2002), pp. 1337-1349.

Varian Medical Systems, Oncology Systems, Portal Vision, Image Guided Radiotherapy, (1999) Brochure.

Partial Supplementary European Search Report mailed Sep. 23, 2008; European Patent Application No. 03808034.7.

Varian, Office Action mailed May 25, 2009, Japanese Patent Application No. 2004-543215.

PCT Search Report, International application No. PCT/US03/22725, International filing date Jul. 22, 2003.

* cited by examiner

IMAGING DEVICE FOR RADIATION TREATMENT APPLICATIONS

FIELD OF THE INVENTION

The present invention pertains in general to radiation medicine. In particular, the invention involves imaging devices.

BACKGROUND

A technique to perform radiation therapy uses a radiotherapy device to target a radiation treatment beam onto a target volume (e.g., a tumor) of a patient. Such, radiation treatment beams emulate from a treatment radiation source, such as a megavoltage x-ray source. Here, the primary purpose of the x-ray source is to provide a sufficient dose of radiation to treat the target volume. Additionally such a radiotherapy device may include a separate imaging device used to image anatomy in the region of the target volume. This imaging device may use an imaging radiation source, such as a kilovoltage x-ray source. A radiation imager or detector is also used to capture the radiation after it passes through the patient. Information obtained from this imager can be used to adjust or verify correct positioning of patient anatomy and particularly of the target volume relative to the treatment beam.

The imaging device including an x-ray source and imager may be attached to a gantry that houses the treatment radiation source. One such design is typically embedded in a wall in a treatment area. In another design, the x-ray source and imager are attached inside a large diameter bearing (e.g., a cylinder) that the patient must enter for treatment.

With these gantry designs the movement of the x-ray source and the imager are limited to the movement of the gantry. That is, the arms that attach the x-ray source and the imager to the gantry are rigidly attached (e.g., stationary) or have limited ability to move in relation to the gantry. Furthermore, they have limited ability to be moved or stored "out of the way" to allow a technician unrestricted access to the patient, especially if the patient is being treated inside the bearing housing the x-ray source and imager. In addition, the inflexible manner in which the x-ray source and imager are attached to the gantry limits the movement of these treatment components independent from the movement of the gantry. For example, when the gantry is rotated to a specific position both components move with it, and the limited positions in which these components can be placed puts constraints on system movement and patient accessibility. Therefore, these designs limit the versatility of positioning an imaging beam and possibly even a treatment beam.

Another major disadvantage of such a system is the unintended consequence of mechanical flexure of the device. That is, the sagging weight of the x-ray source and/or imager may cause a misalignment of the imaging beam relative to the treatment beam. Such misalignment may result in unintended error in placing the target volume within the treatment beam thereby causing unintentional damage to healthy tissue and/or an inadequate dose delivered to the target volume during treatment. The proper targeting of the x-ray source to the treatment area is essential to delivery of the proper dose of radiation to the target volume and to minimize the dose of radiation to healthy tissue. Conventional radiotherapy devices do not have the capability to identify mechanical flexure in real-time and make corrections before administrating the treatment beam.

SUMMARY OF THE INVENTION

A radiotherapy clinical treatment machine is described having a rotatable gantry and an imaging device with articulating robotic arms to provide variable positioning and clearance for radiation treatment applications. According to one aspect of the invention, a first and second robotic arms are pivotally attached to the rotatable gantry, allowing the robotic arms to maneuver independently from the rotatable gantry.

BRIEF DESCRIPTION OF THE DRAWINGS

The invention may best be understood by referring to the following description and accompanying drawings that are used to illustrate embodiments of the invention. In the drawings.

DETAILED DESCRIPTION

In the following description, numerous specific details are set forth to provide a thorough understanding of the invention. However, it is understood that the invention may be practiced without these specific details. In other instances, well-known circuits, structures and techniques have not been shown in detail in order not to obscure the invention.

A radiotherapy clinical treatment machine is described having a rotatable gantry and imaging device with articulating robotic arms to provide variable positioning and clearance for radiation treatment applications. More specifically, a number of design configurations of the articulating robotic arms will be described that enable the positioning and re-positioning of a imaging source and a signal imager to provide versatility in placement and alignment to obtain imaging information useful in radiation treatment to a patient. Each device to be described has the ability to extend and retract the robotic arms to allow open access to the patient. Another aspect of some embodiments of the invention discloses how the variable real-time positioning of the robotic arms also provides improved targeting of the target volume by correcting for mechanical flexure of the device as will be described. In this way, imaging of the patient may be accomplished from a multitude of positions, orientations and directions as a result of the degrees of freedom given the articulating robotic arms, as will be described.

The following description describes embodiments of the invention using radiographic imaging techniques to analyze a target volume, however, it should be understood that the invention is not limited to radiographic imaging techniques, and in alternative embodiments, other imaging techniques (such as, for example, computed tomography (CT), fluoroscopy, computed laminar tomography, etc.), including known imaging techniques using other forms of radiated energy (such as ultrasound RF or light) might also be used by one of ordinary skill in the art, but are not described herein, so as to not obscure the invention.

FIG. 1 illustrates one embodiment of a radiotherapy clinical treatment machine with an imaging device having articulable robotic arms that swing laterally to/from a storing position from/to an imaging position. FIG. 2 illustrates one embodiment of a radiotherapy clinical treatment machine with an imaging device having robotic arms that swing downward to/from a storing position from/to a imaging position. FIG. 3 illustrates one embodiment of a radiotherapy clinical treatment machine with an imaging device having robotic arms that swing to/from a storing position from/to a imaging position. Each design allows for various functional, cost, and/or storage benefits as will be further described below.

Preferred designs of the radiotherapy clinical treatment machine (in FIGS. 1, 2, and 3) include a rotatable e.g. open gantry 202 that can be pivotably attached to a drive stand 203 of the radiotherapy clinical treatment machine 200. The gantry 202 is capable of 360-degree rotation 215 about a centerline 216. Each gantry 202 may also include one or more radiation sources and one or more imagers. Each of FIGS. 1, 2, and 3 show an imager 214 folded into the rotatable gantry 202 to provide more clearance. The imager 214 may be unstowed and positioned beneath the patient (not shown), or more specifically, positioned opposite a treatment radiation source 212 to provide imaging of the patient using the treatment beam, as will be described.

Figure 1A:
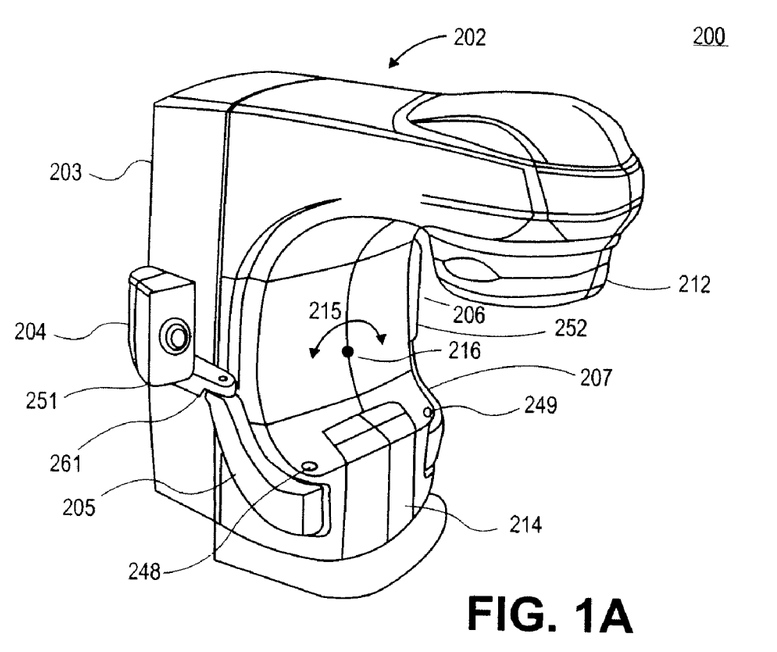
FIG. 1 is an illustration in one embodiment of a radiotherapy clinical treatment machine with an imaging device having robotic arms that swing laterally to an imaging position from a clearance position.

FIG. 1A is a perspective view illustrating one embodiment of the rotatable open gantry 202 having articulating robotic arms (205 and 207) each attached to pivot points 248 and 249 at the base of the rotatable gantry 202. The opposite end of arm 205 is pivotally attached at a source end 251 to an imaging source 204. The opposite end of arm 207 is pivotally attached at an imaging end 252 with an imaging detector 206. For imaging, the robotic arms (205 and 207) swing outward into an adjustable imaging position along a defined trajectory 272, as shown in FIG. 1B.

In this way, the robotic arms (205 and 207) can extend and retract for positioning and clearance. In addition, the source end 251 and the imaging end 252 may contain any number of pivot points, from single plane pivots to ball joints, having 360 degrees of rotation for positioning the imaging source 204 and imaging detector 206. In this way, the robotic arms (205 and 207) may be independently articulated into alignment for the imaging detector 206 to receive an image of the patient from the imaging source 204.

Figure 1B:
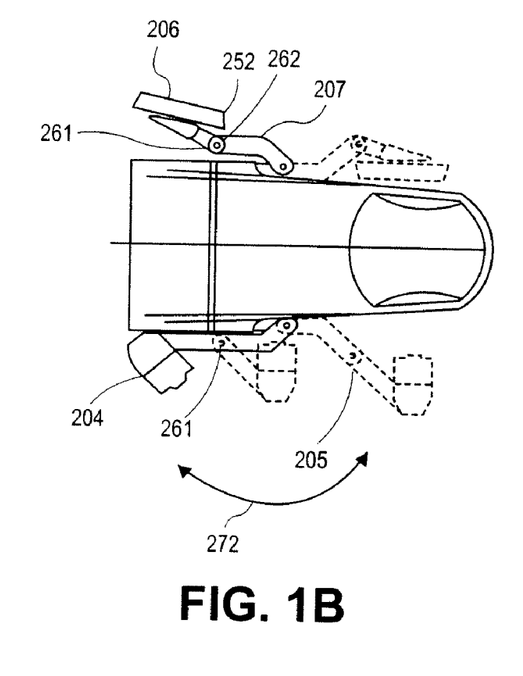
Figure 1C:
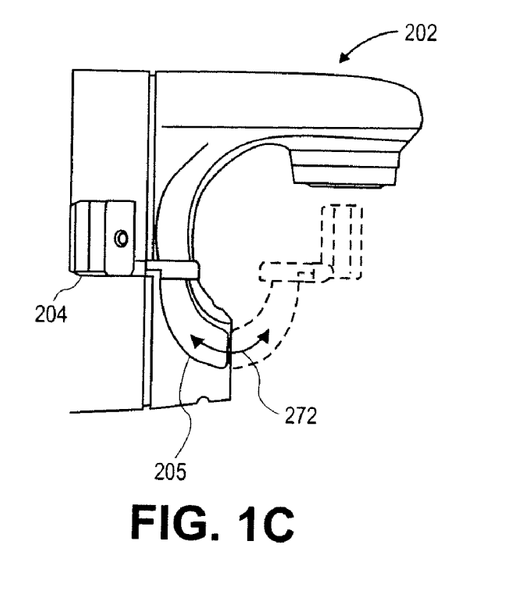

FIG. 1B is a top view and FIG. 1C is a side view of the machine 200 illustrating the swinging motion of robotic arms 205 and 207 to position the radiation source 204 and imager 206 for positioning and clearance. Each arm (205 and 207) also includes pivot points 261 and 262 that add to the maneuverability and positioning of the arm. FIG. 1C also illustrates that each arm 205 and 207 may be curved to conform to the shape of the gantry 202 so as to maximize patient clearance.

Figure 2A:
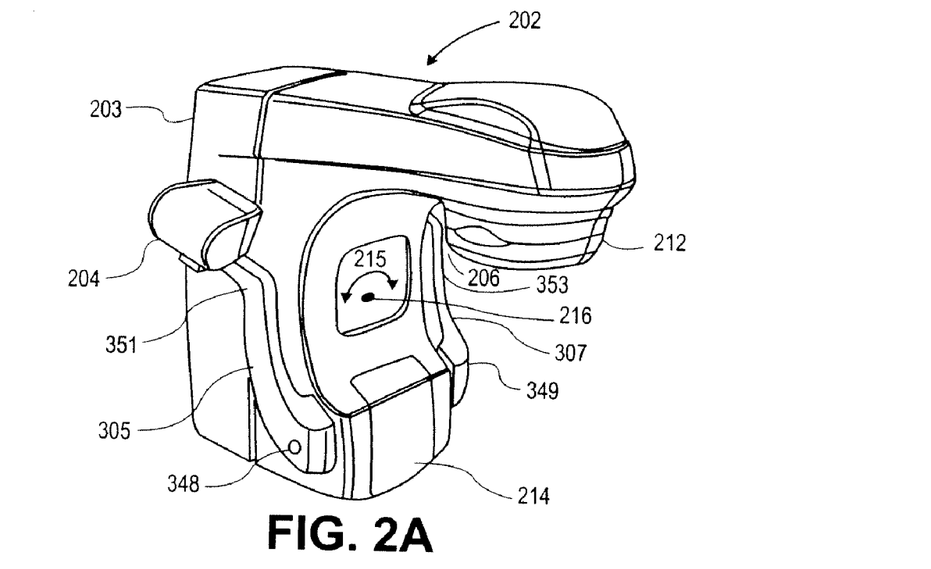
FIG. 2 is an illustration in one embodiment of a radiotherapy clinical treatment machine with an imaging device having robotic arms that swing downward to an imaging position from a clearance position.

FIG. 2A is a perspective view illustrating one embodiment of the rotatable open gantry 202 having articulating robotic arms (305 and 307) each attached to a pivot point 348 and 349 at the base of the rotatable gantry 202. The arm 305 is fixedly attached at a source end 351 to the radiation source 204. The arm 307 is pivotally attached at an imaging end 353 with the imager 206. For imaging, the robotic arms 305 and 307 swing downward into an imaging position along a plane of motion (352), as shown in FIG. 2C.

In this way, the robotic arms (305 and 307) can extend and retract for positioning and clearance. It should be appreciated that because the arm 305 is fixedly attached to the radiation source 204, the design is simple and therefore less costly. However, in alterative embodiments, the arm 205 may be pivotally attached to the radiation source 204. In addition, the source end 351 and the imaging end 353 may contain any number of pivot points, from single plane pivots to ball joints, having 360 degrees of rotation for positioning the imaging source 204 and imaging detector 206. Therefore, the robotic arms (305 and 307) may be independently articulated into alignment for the imaging detector 206 to receive an image of the patient using the imaging source 204.

Figure 2B:
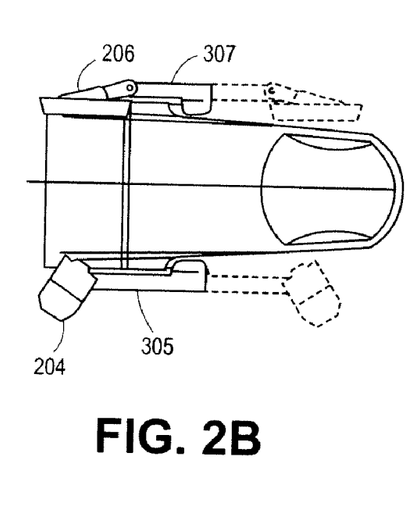
Figure 2C:
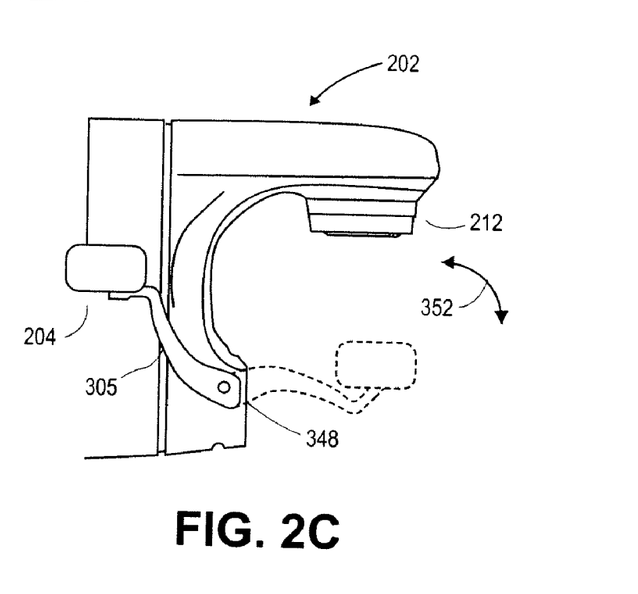

FIG. 2B is a top view and FIG. 2C is a side view of the machine 200 illustrating the swinging motion of robotic arms 305 and 307 to position the radiation source 204 and imager 206 from positioning and clearance.

Figure 3A:
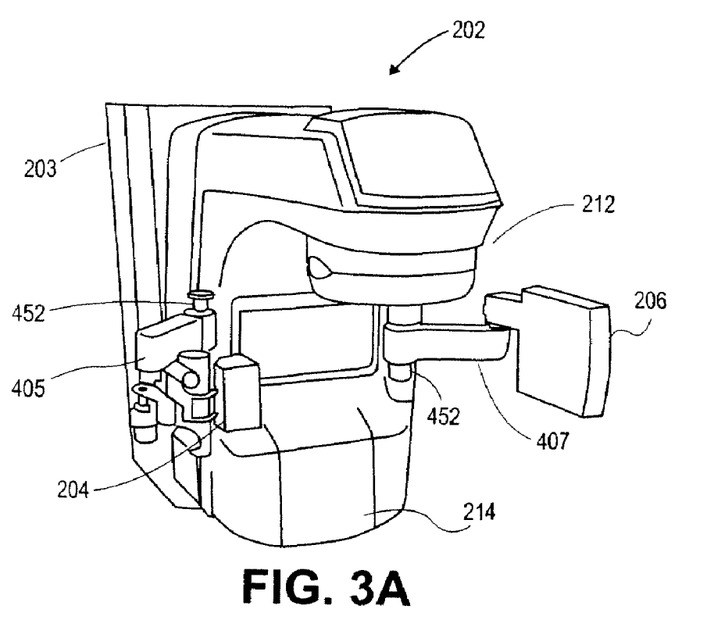
FIG. 3 is an illustration in one embodiment of a radiotherapy clinical treatment machine with an imaging device having robotic arms that swing to an imaging position from a clearance position.

FIG. 3A is a perspective view illustrating one embodiment of the rotatable open gantry 202 having articulating robotic arms (405 and 407) each attached to a pivot point at a midsection (452) of the rotatable gantry 202. The arm 405 is pivotally attached at a source end 451 to the radiation source 204. The arm 407 is pivotally attached at an imaging end 453 to an imager 206.

Figure 3B:
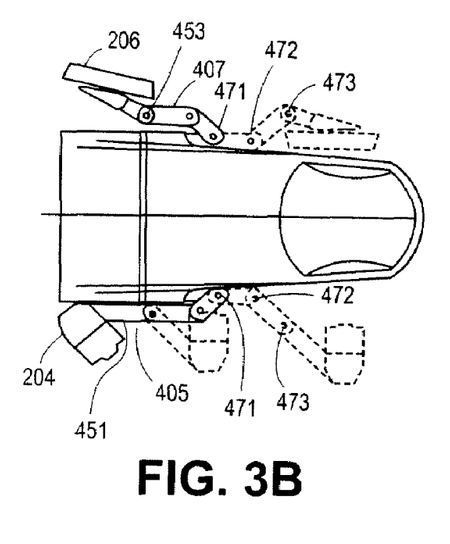
Figure 3C:
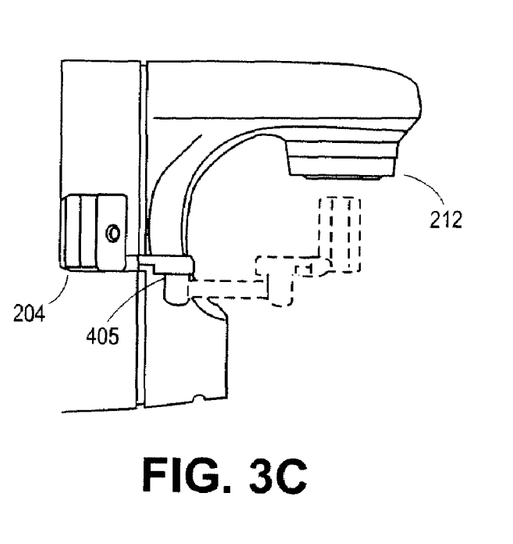

FIG. 3B is a top view and FIG. 3C is a side view of the machine 200 illustrating the swinging motion of robotic arms 405 and 407 to position the radiation source 204 and imager 206. As shown in FIG. 3B, the robotic arms 405 and 407 may pivot at three points 471, 472, and 473 along two independent axes in a plane. For imaging, the robotic arms 405 and 407 swing outward to an adjustable imaging position, as shown in FIG. 3C.

Each pivot point 248, 249, 261, 262, 348, 349, 471, 472, and 473, can be a set of sliding mechanisms that include gears and motors that are well known to one of ordinary skill in the art. The result of such articulation can be to place the imaging detector 206 in alignment with, and at a distance from, the imaging source 204 with the target volume positioned in between.

Therefore, adjustments could be made to place the imaging detector 206 and source 204 at various distances and angles from the patient with the articulating robotic arms 407 and 407. In this way, each of the robotic arms may be positioned independently and/or in conjunction with the movement (or non-movement) and positioning of the rotatable gantry 202.

Figure 4:
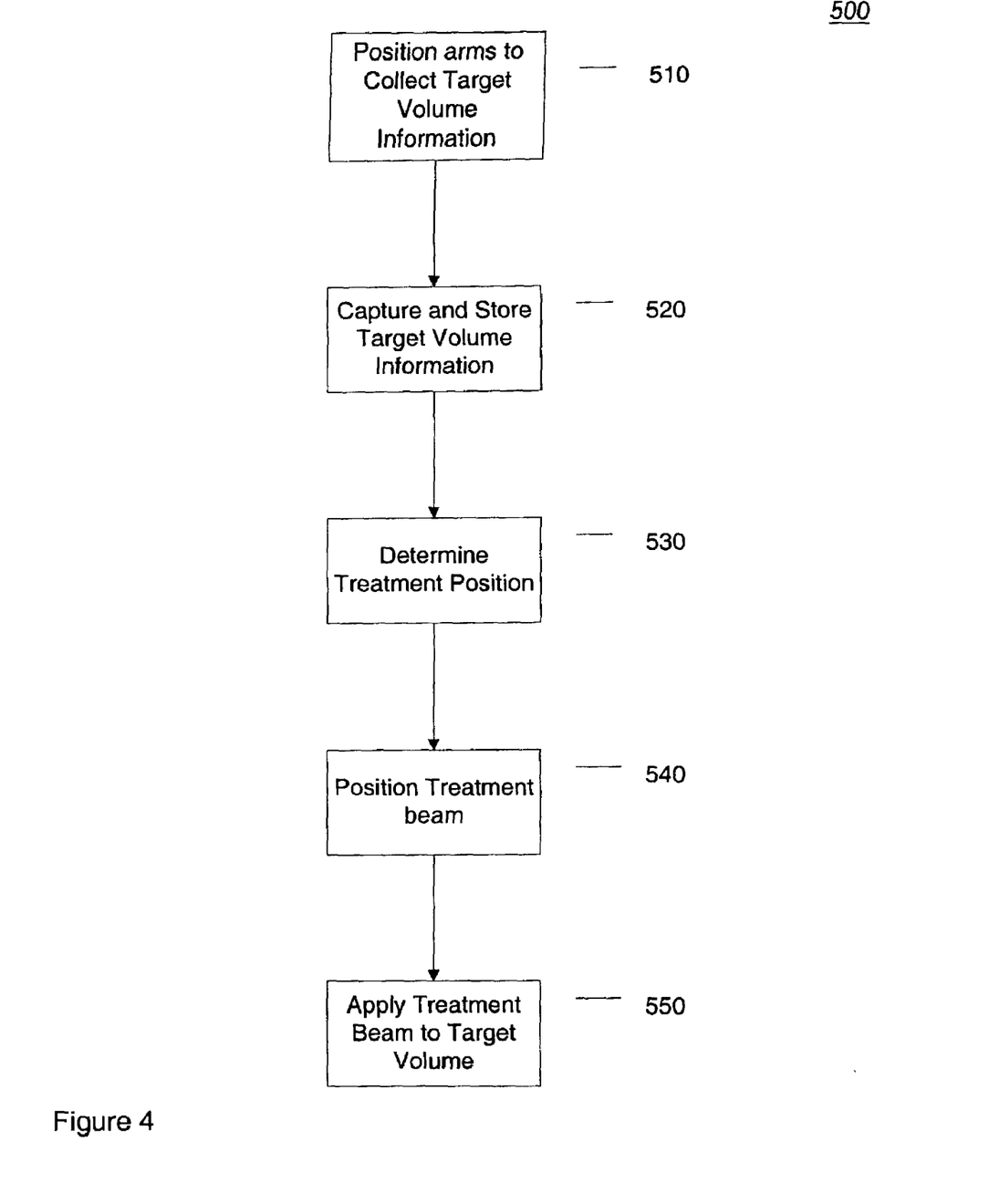
FIG. 4 is an illustration in one embodiment of a process flow of using the articulating robotic arms to provide a treatment.

FIG. 4 illustrates an exemplary process flow (500) of using the articulating robotic arms to provide a treatment according to one embodiment. At block 510, the robotic arms are positioned to collect target volume information, such as the shape, size, and location of a tumor in the patient, or the position of an e.g. anatomical landmark or other marker. At block 520, the target volume information is captured and stored, for example, in a computer (that will be further described below). Based on the target volume information, one or more appropriate treatment positions for the device 200 may be determined to apply a radiation treatment beam to the target volume (at block 530). The device 200 is maneuvered to the treatment position (at block 540) and the treatment beam is applied at the correct dosage to the target volume (at block 550).

In one embodiment, the configuration designs of FIGS. 1, 2, and 3 allow imaging radiation source 204 to emit radiation at a first energy level to radiate a target volume along a first axis to provide target volume data to the imaging detector 206. Target volume data from the imaging detector 206 can direct treatment radiation source 212 to emit radiation at a second energy level along a second axis to provide therapeutic radiation to the target volume and verification information to the treatment imaging detector 214.

Imagers can generally provide high quality imaging from one radiation energy range and lower quality imaging from other radiation energy ranges. The first energy level, for example, can be in the kilovolt energy range (kV) and the second energy level, for example, can be in the megavolt energy range (MV). The radiation source 212 can generate an electron beam, generally in the 4 to 25 megavolt range, to provide electrons or X-rays to a volume within a patient undergoing treatment. The imaging detector 214 can display radiographic information from the megavolt radiation sufficient to provide verification that the target volume is being radiated.

The imaging detector 206 can receive X-rays in the kV range to provide more accurate target volume data on the size, shape, and location of the target volume. Repeated X-ray shots with kV energy that alternate with MV radiation can reduce target error such as by directing a continuous adjustment of the beam shaping by a dynamic multileaf collimator and by providing targeting information to the MV radiation source.

In one embodiment, after a target volume definition has been provided by the imaging radiation source 204, the imaging detector 206 and the imaging radiation source 204 can be retracted for clearance via their respective robotic arms. The gantry 202 can be rotated into position to administer a treatment beam from the radiation source 212, based on the target volume definition.

The accuracy of target volume information may be improved by placing internal seeds to act as markers for the target volume. Placement of these markers can be accomplished by performing a needle biopsy. This procedure is normally performed to gain tumor grading information to plan the therapy. These markers can provide higher contrast for the imaging detector 206 for some tissues that might otherwise be difficult to discern. The use of internal seeds may determine a more accurate location of the target volume and/or edges of the target volume. The seeds may be placed away from the target in a location from which the target position and/or motion may be determined. Target volume data can be stored and recalled later to provide anatomical landmark definition to enhance position information on the target volume during radiotherapy.

A treatment bench (not shown) can be positioned adjacent to the gantry 202 to place the patient (and target volume) within the range of operation for the radiation sources 204 and 212, and the image detectors 206 and 214. In one embodiment, the bench can be capable of translating in multiple planes for positioning and re-positioning the patient and therefore the target volume, based on the target volume data.

Figure 5:
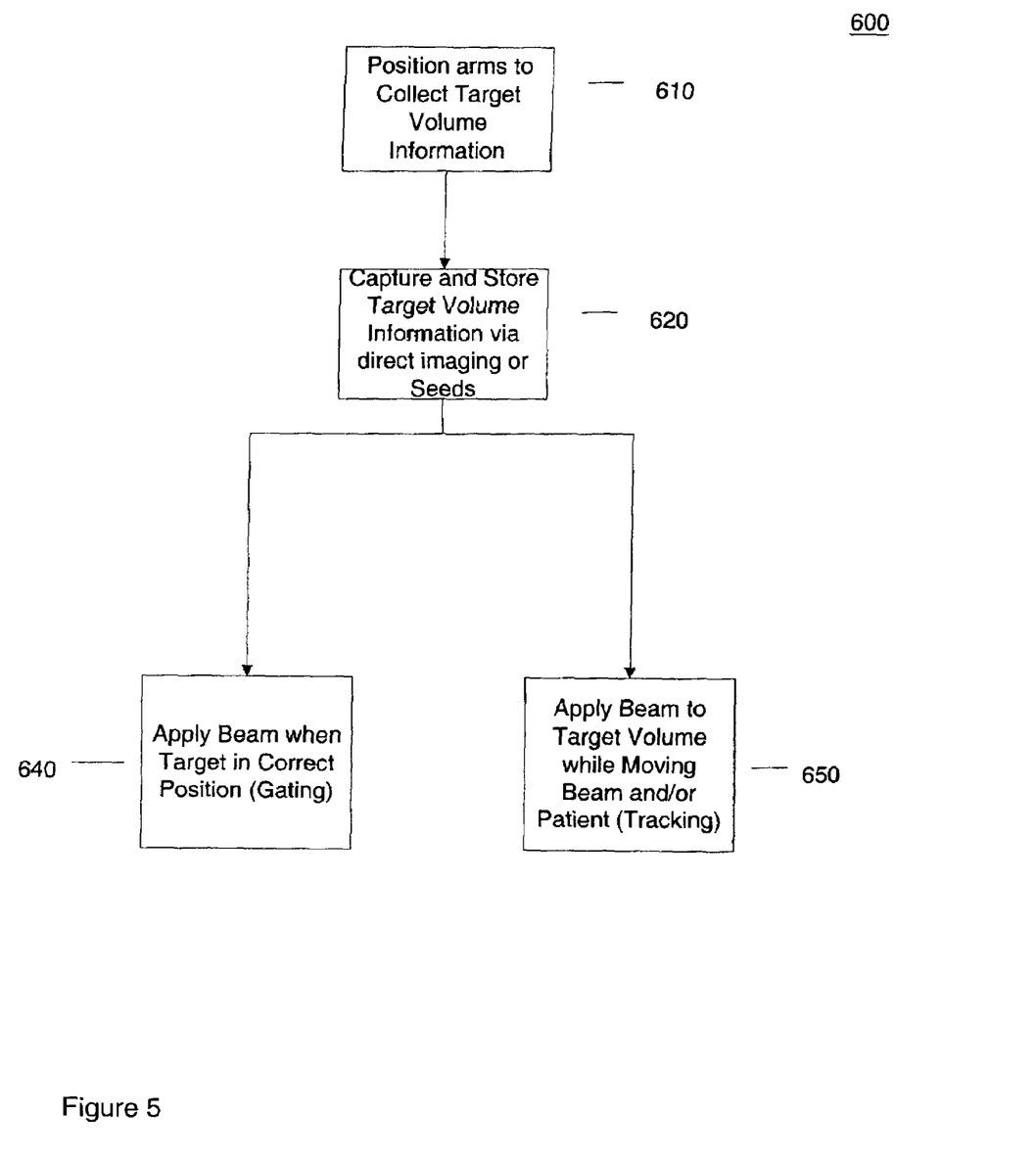
FIG. 5 illustrates a process flow of using the articulating robotic arms to provide a treatment according to one embodiment.

FIG. 5 illustrates a process flow (600) of using the articulating robotic arms to provide a treatment according to one embodiment. At block 610, the robotic arms are positioned to collect target volume information, such as the shape, size, and location of a tumor in the patient, or the position of an e.g. anatomical landmark or other marker. At block 620, the target volume information is captured and stored, for example, in a computer (that will be further described below). As discussed, the target volume information may be captured by direct imaging of the target volume and/or by imaging the markers. Thereby, the treatment beam may be positioned and applied (at block 640) when the target is in the correct position (gating), or the treatment beam may be positioned and applied to the target volume while the treatment beam and/or the patient is moving to track tumor motion (at block 650).

In one embodiment, target volume data can be delivered and stored to a general or special purpose computer system. The computer system may be coupled to the gantry 202 directly or across a network connection, and each of the translatable devices (radiation sources 204 and 212, and imagers 206 and 214,) and also, the treatment bench 218. In one embodiment, software in the computer system can generate a representation of the target volume based on digital image data provided by the imaging detector 206. Following a pre-determined treatment plan and/or the image data, irradiation of the target volume from selected radial locations can occur. The control software in the computer can be used to operate the radiotherapy clinical treatment machine 200, such as, for example, to rotate and translate the above devices 202, 204, 206, 212, and 214, to position the target volume in line with the treatment beam that is shaped to the target volume.

In one embodiment, the computer can merge the image data generated from at least two different radial locations into a stereoscopic representation of the target volume. The stereoscopic representation can be used to determine, in 3-D, the location of the target volume, or some volume associated with it, such as an anatomical structure and/or marker. Thereby, allowing the target beam to target the target volume.

The articulable design and motion of the robotic arms (205, 207, 305, 307, 405, and 407) provide independent positioning of the robotic arms to improve the treatment process. For example, the robotic arms may be positioned (via robotic motions) to extend the distance between a radiation source and an imager. That is, to extend the normal distance between the radiation source 204 and imaging unit 206 while performing target volume analysis and/or treatment (e.g., positioning the distance between source and imager to approximately 150 cm). This ability to extend the distance provides for varying needs of patient or equipment clearance and allows for different imaging resolutions and imaging field coverage.

The robotic arms may also be positioned (i.e., contracted) to provide higher resolution than would otherwise be possible using stationary arms. For example, the robotic arms may be maneuvered to shorten the distance between the imager 206 and radiation source 204 (e.g., to approximately 130 cm) to provide for high resolution imaging of the target volume.

The robotic arms may also be positioned to collect data from a location other than the target volume to perform treatment. In this embodiment, one or both of the imaging source 204 and the detector 206 may be off-set longitudinally from isocenter and thereby monitor intra-fraction motion away from isocenter (and the target volume). For example, the source and detector can be positioned to monitor chest wall or diaphragm motion associated with patient breathing while treating a volume in the upper thorax or lower abdomen. This motion information may be used to control the timing or positioning of the treatment beam while treatment proceeds. In embodiments with sufficient articulation, the imaging source and imaging detector can be offset longitudinally and at any longitudinal position from the gantry can also be extended towards or retracted away from each other as described above.

The robotic arms may also be positioned at unequal distances from the gantry. At times it may be beneficial to have the arms an unequal distance from the gantry to provide additional versatility to the imaging process. For example, a first arm positioning an imaging detector 90 cm from the gantry may capture radiation from an imaging source, on a second arm, 130 cm from the gantry. This gives added flexibility in the types of images that may be taken. For example, in some cases this will allow simultaneous imaging of isocenter and another area of interest away from isocenter, such as the diaphragm.

In any embodiment, the first and second arms may then be repositioned so that, for example, the imaging detector and the imaging source are at a first relative position for a first image, and then at a second relative position angularly offset from the first position for a second image. In this way, a stereoscopic representation of the target volume may be generated to determine target location in three dimensions. This may be accomplished by motion of one or more pivot points on one or both arms. In one embodiment, one pivot point, e.g. a pivot point nearest the imaging source and/or nearest the imaging detector may use a sliding mechanism.

The robotic arms may also be positioned to extend for a large field-of-view CT. For example, the imager may be off-set laterally, with an edge of active imager screen at the center of a source's axis. The computer may use a combination of these positions to describe a large field-of-view cone beam computed tomography (CBCT). In this way, a relatively small imager could be used to provide an image in 3-D, which would not otherwise be readily available using an imager of this size. Furthermore, upon performing a full rotation about the target volume, the imager may obtain an image of the entire target volume that typically would be available to an imager approximately twice its size.

In one embodiment, the imaging source 204 can be rotated about the target volume for CT single slice or multiple CT images using a fan x-ray beam, or by using a cone x-ray beam where volumetric information can be constructed. In some embodiments, the arms can move such that the image detector and image source perform at least a partial rotation about the volume to obtain a CT reconstruction without necessarily moving the gantry. Also, if a partial data set is acquired from a limited number of images taken at specific angles around the target volume, enough information can be obtained with the help of previously acquired volumetric information to provide the three dimensional reconstruction of the anatomy of interest. As a result, imaging from the radiation source 205 X-rays can provide targeting information to accurately direct the therapeutic X-rays to the target volume from any angle while effectively excluding healthy tissue from injury. Furthermore, the imaging radiation source 204 and detector 206 can be operated either in a continuous or pulsed manner to provide a real time or quasi-real time fluoroscopic image of moving internal anatomy. This fluoroscopic image can also be used to provide information to track the motion of anatomy being treated. As is generally known, normal respiration or unwanted voluntary or involuntary patient movement may cause such motion. This motion tracking information can in turn be used to adjust treatment parameters, track the target volume with the treatment beam, and/or gate the treatment beam off and on such that the anatomy intended to be treated is always in the intended position within the treatment beam.

It should be understood that the arrangements described herewith for positioning the robotic arms having the imager and radiation source is illustrative of only a few positions and advantages of having articulating robotic arms on a gantry, and, the invention is not limited by the positions described. It is to be further appreciated that the various embodiments of articulating the robotic arms can be accomplished with any combination of pivot points, either 2-dimensional (e.g., pivot in a plane), 3-dimensional (e.g., ball joints), or sliding mechanisms, and other well know techniques to provide positioning and clearance. As a further example, a source and detector can move in substantially parallel planes, in opposite directions, to perform laminar tomography.

It should also be understood that although embodiments of the invention are described as having arms including either the image detector or imaging source, in alternative embodiments each arm may have one or more of either or both of sources and/or image detectors. The imaging sources and imaging detectors may be placed at any position on the arms. For example, in one embodiment with two imaging sources and two imaging detectors, both arms may have one of each, with the two imaging detectors placed in the position nearest the treatment source on both arms, and the two imaging sources placed in the lower position on each arm. In this way, in applications where the imaging occurs during treatment, the amount of backscattered radiation from the treatment beam detected by the imaging detectors may be reduced. The number of image detectors and imaging sources to be used may be based on factors such as simplicity, cost, and versatility.

In one embodiment, an arm attached to the gantry 202 may have two image detectors. These two detectors may capture radiation from one or more imaging sources. For example, the imaging source(s) and detectors may be off-set radially about the patient, to provide data to the computer to generate a stereoscopic representation of a target volume, as described above. Here, the imaging detector may be at a different distant from the gantry than the imaging source(s). Therefore, both the imaging detector and imaging source(s) are rotated at an angle, for the detector to capture the radiation of the imaging source.

In another embodiment, one arm may have a single imaging detector that captures radiation from one or more imaging sources. For example, if the single imaging detector receives radiation from a single source, the imaging detector and/or imaging source might be repositioned to receive radiation from varying positions and angles. Thereby, providing target volume data to generate a stereoscopic representation of the target volume, as described. Furthermore, a single imaging detector on one arm may also capture radiation from two spaced apart (possibly pulsing alternately) radiation sources on the other arm. Where the imaging detector is positioned and angled accordingly, to again, provide target volume data to generate a stereoscopic representation of the target volume.

In one embodiment, an image from a single source/detector pair together with an image taken during treatment from e.g. imager 214 may be used to form a stereoscopic representation. In a further embodiment, the image detector might be a multiple-energy imaging unit capable of receiving and displaying imaging information from multiple energy sources. For example, one of the energies can be a source of megavoltage x-ray energy and another a source of kilovoltage x-ray energy, both of which can alternately activate the multiple-energy imaging unit for high quality verification imaging and high quality target volume imaging, respectively.

It is to be further appreciated that the device 200 may also correct for mechanical flexure of the radiation source and imaging unit to improve image quality. Due to the weight of the radiation source and imager, the imaging beam may be misaligned causing error. In one embodiment, the imager-source stability is defined by projecting the x-ray beam past a set of markers of known fixed position, while rotating the gantry 360 degrees, and determining the difference from the ideal position by measuring the resulting lateral and longitudinal shift in the image. Likewise, unwanted play or movement in any particular joint within the arm may be directly measured by a suitable sensor (for example encoder or potentiometer) incorporated in the mechanism associated to that joint. Either or both types of the foregoing information is used by a feedback control system to properly align the sagging radiation source and image detector in real-time during imaging.

Thus, a radiotherapy clinical treatment machine with a rotatable open gantry having articulating robotic arms has been described. It should be appreciated that such robotic arms provide variable positioning and clearance for e.g. effective administration of oncology radiation therapy to a patient. The articulating robotic arms operating independently and/or in conjunction with the movement of the rotatable gantry. Furthermore, the machine includes logic to detect and correct any mechanical flexure of the device in real-time before administrating the treatment beam. Thereby, providing better images for more accurate treatment and to minimize targeting of healthy tissue.

It should be appreciated that that more or fewer processes may be incorporated into the methods illustrated in FIGS. 4 and 5 without departing from the scope of the invention and that no particular order is implied by the arrangement of blocks shown and described herein. It further will be appreciated that the method described in conjunction with FIGS. 4 and 5 may be embodied in machine-executable instructions (e.g. software). The instructions can be used to cause a general-purpose or special-purpose processor that is programmed with the instructions to perform the operations described. Alternatively, the operations might be performed by specific hardware components that contain hardwired logic for performing the operations, or by any combination of programmed computer components and custom hardware components. The methods may be provided as a computer program product that may include a machine-readable medium having stored thereon instructions that may be used to program a computer (or other electronic devices) to perform the methods. For the purposes of this specification, the terms "machine-readable medium" shall be taken to include any medium that is capable of storing or encoding a sequence of instructions for execution by the machine and that cause the machine to perform any one of the methodologies of the present invention. The term "machine-readable medium" shall accordingly be taken to included, but not be limited to, solid-state memories, optical and magnetic disks, and carrier wave signals. Furthermore, it is common in the art to speak of software, in one form or another (e.g., program, procedure, process, application, module, logic . . . ), as taking an action or causing a result. Such expressions are merely a shorthand way of saying that execution of the software by a computer causes the processor of the computer to perform an action or produce a result.

It should be understood that although specific illustrative embodiments have been described, portions of one embodiment might be used in combination with portions of one or more other embodiments. Therefore, the illustrative embodiments of the various design components may be interchanged based on varying factors, such as cost, simplicity, and versatility. As one example, in one embodiment, one arm may have more pivot points than the other arm. For example, it may be desirable to provide, e.g., the imaging detector with greater articulation than the imaging source. This provides for greater flexibility in meeting function and cost objectives.

While the invention has been described in terms of several embodiments, those skilled in the art will recognize that the invention is not limited to the embodiments described. For example, while a radiotherapy apparatus has been shown, the invention may find use in any application where it is desirable to perform imaging as described herein. The method and apparatus of the invention can be practiced with modification and alteration within the scope of the appended claims. The description is thus to be regarded as illustrative instead of limiting on the invention.

What is claimed is:

1. An apparatus, comprising:
   a rotatable gantry including a treatment source;
   a first arm coupled to the rotatable gantry at a first coupling point, and the arm having a pivot point separate from the first coupling point;
   an imaging source coupled to a source end of the first arm;
   a different second arm coupled to the rotatable gantry at a different second coupling point; and
   an image detector coupled to the imaging end of the second arm.

2. The apparatus of claim 1, wherein the first arm and the second arm extend and maneuver independent from the rotatable gantry.

3. The apparatus of claim 1, wherein the first arm and the second arm extend independently to an imaging position from a retracted position.

4. The apparatus of claim 3, wherein the first arm and the second arm swing laterally into the imaging position from the retracted position.

5. The apparatus of claim 3, wherein the first arm and the second arm swing downward into the imaging position from the retracted position.

6. The apparatus of claim 1, wherein the imaging source is at a different distance from the gantry than the image detector, wherein the imaging source is pivotally positioned to target the image detector, and the image detector is pivotally positioned to capture an imaging beam from the imaging source.

7. The apparatus of claim 1, wherein the image detector provides target volume information.

8. The apparatus of claim 7, further comprising:
   a computer to position a treatment beam based on the target volume information.

9. The apparatus of claim 1, further comprising:
   a computer having a mechanical flexure feedback control component to correct a mechanical flexure of the imaging source and a mechanical flexure of the imager.

10. The apparatus of claim 1, wherein the pivot point is at the first coupling point.

11. The apparatus of claim 1, wherein the pivot point pivotally couples the imaging source to the source end of the first arm.

12. The apparatus of claim 1, wherein the pivot point is between the first coupling point and the source end of the first arm.

13. The apparatus of claim 1, wherein the first coupling point for the first arm is a first pivot point, and the pivot point is a second pivot point.

14. The apparatus of claim 13, wherein the different second coupling point for second arm is a third pivot point.

15. The apparatus of claim 1, wherein the second arm is separate from the rotatable gantry.

16. A method to perform a clinical treatment, comprising:
   independently positioning a first arm and a second arm with respect to where the first and second arm are coupled to a rotatable gantry to receive target volume data, the first arm coupled to the rotatable gantry at a first coupling point, and the first arm having a pivot point separate from the first coupling point, the second arm coupled to the rotatable gantry at a second coupling point, wherein the first arm is positioned from a clearance position and wherein the gantry includes a treatment source;

wherein the first arm comprises a diagnostic radiation source and the second arm comprises an imager;
wherein the treatment source comprises a source of treatment radiation separate from the diagnostic radiation source;
determining a treatment position for a treatment beam based on the target volume information;
applying the treatment beam upon maneuvering the treatment source to the treatment position.

17. The method of claim 16, wherein the positioning the first arm and the second arm includes positioning an image detector on the first arm to receive radiation from an imaging source on the second arm.

18. The method of claim 17, wherein the target volume data is based on the radiation received by the image detector.

19. The method of claim 17, wherein the positioning includes extending the first and second arms to provide higher resolution.

20. The method of claim 17, wherein the positioning includes extending the first and second arms for large field-of-view computed tomography.

21. The method of claim 17, wherein the positioning includes correcting for mechanical flexure.

22. The method of claim 17, wherein the target volume information is based on intra-fraction motion away from a target volume.

23. The method of claim 16, wherein the positioning the first arm and the second arm includes positioning an image detector on the first arm to receive radiation from a first and a second radiation source.

24. The method of claim 16, wherein the determining is based on generated stereoscopic information.

25. An apparatus, comprising:
a gantry having a treatment source;
an imaging source to emit imaging radiation on a target volume;
an imaging means to receive the radiation from the imaging source; and
means for positioning the imaging source and the imaging means, wherein the means for positioning includes the gantry pivotally coupled to the imaging source and imaging means at coupling points, wherein the means for positioning includes a first arm separate from the gantry, the first arm coupled to the gantry at a first coupling point, the first arm including a pivot point separate from the coupling point and including the imaging source, wherein the means for positioning includes a second arm separate from the gantry, the second arm coupled to the gantry at a second coupling point, and the second arm having the imaging means, and wherein the positioning includes transitioning between a clearance position and an imaging position.

26. The apparatus of claim 25, wherein the means for positioning swings the imaging source downward into the imaging position.

27. The apparatus of claim 25, wherein the means for positioning swings the imaging means outward into the imaging position.

28. The apparatus of claim 25, wherein the means for positioning contracts the imaging means to provide a higher resolution.

29. The apparatus of claim 25, wherein the means for positioning extends the imaging means to provide a larger image field of view.

30. The apparatus of claim 25, further comprising:
a computing means to correct a mechanical flexure of the imaging source.

31. An apparatus, comprising:
a rotatable gantry including a treatment source;
a first arm coupled to the rotatable gantry at a first coupling point, and having a pivot point separate from the first coupling point; and
a different second arm coupled to the rotatable gantry at a different second coupling point;
a plurality of imaging sources coupled to the first arm; and
an image detector coupled to the second arm, the image detector to receive radiation from the plurality of radiation sources.

32. The apparatus of claim 31, wherein a first of the plurality of imaging sources is a kilovoltage radiation source.

33. The apparatus of claim 31, wherein the image detector is a multi-energy imager.

34. The apparatus of claim 31, wherein the first arm extents to an imaging position from a clearance position.

35. An apparatus, comprising:
a rotatable gantry including a treatment source;
a first arm coupled to the rotatable gantry at a first coupling point, and the first arm having a first pivot point separate from the coupling point;
an imaging source coupled to a source end of the first arm;
a second arm coupled to the rotatable gantry at a different second coupling point, the second arm having a second pivot point; and
an image detector coupled to the imaging end of the second arm.

36. The apparatus of claim 35, wherein the first pivot point is between the first coupling point and the source end of the first arm, and wherein the second pivot point is between the second coupling point and imaging end of the second arm.

37. The apparatus of claim 35, wherein the first pivot point is at the first coupling point.

38. The apparatus of claim 37, wherein a third pivot point pivotally couples the imaging source to the source end of the first arm.

39. The apparatus of claim 38, wherein a fourth pivot point is between the coupling point and the source end of the first arm.

40. The apparatus of claim 39, wherein the second pivot point is at the second coupling point.

41. The apparatus of claim 40, wherein a fifth pivot point pivotally couples the image detector to the imaging end of the second arm.

42. The apparatus of claim 41, wherein a sixth pivot point is between the coupling point and the imaging end of the second arm.

43. An apparatus, comprising:
a rotatable gantry including a treatment source;
a first arm coupled to the rotatable gantry at a first coupling point, and the first arm having three pivot points;
an imaging source coupled to a source end of the first arm;
a second arm coupled to the rotatable gantry at a different second coupling point; and
an image detector coupled to an imaging end of the second arm.

44. The apparatus of claim 43, wherein the first arm includes a first pivot point at the first coupling point, a second pivot point coupling the imaging source to the source end of the first arm, and a third pivot point between the first coupling point and the source end of the first arm.

45. An apparatus, comprising:
a rotatable gantry including a treatment source;
a first arm coupled to the rotatable gantry at a first coupling point, and the first arm having a pivot point separate from the coupling point;
an imaging source coupled to a source end of the first arm;
a second arm coupled to the rotatable gantry at a second coupling point, the second arm having three pivot points; and
an image detector coupled to an imaging end of the second arm.

46. The apparatus of claim 45, wherein the second arm includes a first pivot point at the second coupling point, a second pivot point coupling the image detector to the imaging end of the second arm, and a third pivot point between the second coupling point and the imaging end of the second arm.

47. An apparatus comprising:
a rotatable gantry including a treatment source;
a first arm coupled to the rotatable gantry at a first coupling point, and having a pivot point separate from the first coupling point, the first arm having at least one radiation source;
a second arm coupled to the rotatable gantry at a second different coupling point, the second arm having a first radiation detector at a first location, and a second radiation detector at a second location, the first and second radiation detectors to capture radiation from the at least one radiation source, and wherein the first and second radiation detectors are off-set radially from the at least one radiation source to provide data to generate a stereoscopic representation of a target volume.

* * * * *

UNITED STATES PATENT AND TRADEMARK OFFICE
CERTIFICATE OF CORRECTION

PATENT NO.      : 7,657,304 B2  Page 1 of 1
APPLICATION NO. : 10/264630
DATED           : February 2, 2010
INVENTOR(S)     : Mansfield et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1475 days.

Signed and Sealed this

Thirtieth Day of November, 2010

David J. Kappos
*Director of the United States Patent and Trademark Office*